(12) United States Patent
Shouda et al.

(10) Patent No.: US 7,805,928 B2
(45) Date of Patent: Oct. 5, 2010

(54) SYSTEM FOR CONTROLLING EXHAUST GAS SENSOR HAVING HEATER

(75) Inventors: Hirofumi Shouda, Toyota (JP); Eijirou Yamada, Hekinan (JP)

(73) Assignee: Denso Corporation, Kariya (JP)

( * ) Notice: Subject to any disclaimer, the term of this patent is extended or adjusted under 35 U.S.C. 154(b) by 720 days.

(21) Appl. No.: 11/712,991

(22) Filed: Mar. 2, 2007

(65) Prior Publication Data
US 2007/0271904 A1 Nov. 29, 2007

(30) Foreign Application Priority Data

Apr. 6, 2006 (JP) ............... 2006-104856
May 30, 2006 (JP) ............... 2006-149163

(51) Int. Cl.
*F01N 3/00* (2006.01)
(52) U.S. Cl. ............... 60/285; 60/274; 60/276; 60/277; 60/284; 60/320; 123/688; 123/690; 123/697; 219/492; 219/494; 73/114.71; 73/114.75
(58) Field of Classification Search ........... 60/276, 60/277, 284, 285, 286, 320, 274; 123/688, 123/690, 697; 219/492, 494; 73/114.71, 73/114.75
See application file for complete search history.

(56) References Cited

U.S. PATENT DOCUMENTS

| | | | |
|---|---|---|---|
| 6,345,499 B1 * | 2/2002 | Nishimura et al. | ............ 60/277 |
| 6,476,364 B1 * | 11/2002 | Shimamura et al. | ......... 219/494 |
| 6,543,220 B2 * | 4/2003 | Yoshida et al. | ................ 60/285 |
| 6,696,673 B2 * | 2/2004 | Okamoto | .................... 219/494 |
| 6,781,098 B2 | 8/2004 | Toyoda | |
| 6,823,722 B2 * | 11/2004 | Yamazaki et al. | .............. 73/73 |
| 6,898,927 B2 * | 5/2005 | Morinaga et al. | ............. 60/284 |
| 7,047,728 B2 * | 5/2006 | Yasui | .......................... 60/285 |

(Continued)

FOREIGN PATENT DOCUMENTS

JP 6-90167 11/1994

(Continued)

OTHER PUBLICATIONS

Office Action dated Mar. 19, 2010 issued in corresponding Japanese Application No. 2006-104856 with an at least partial English-language translation thereof.

*Primary Examiner*—Binh Q Tran
(74) *Attorney, Agent, or Firm*—Nixon & Vanderhye, PC

(57) ABSTRACT

An exhaust gas sensor for detecting oxygen concentration in exhaust gas is disposed in an exhaust pipe of an internal combustion engine. The sensor including a heater is controlled by a system that includes an electronic control unit. Water vapor contained in the exhaust gas is condensed on the sensor when the exhaust gas temperature is low. If the water condensation occurs while the sensor is heated by the heater, a sensor element may be cracked due to local cooling by the condensed water. To avoid the water condensation, the exhaust gas temperature is raised by retarding ignition timing of the engine for a certain period after the engine is started. After the exhaust gas is heated to a certain level, the sensor is heated. Alternatively, heating of the sensor is prohibited until the exhaust gas temperature becomes to a level at which no water condensation occurs. Thus, the cracking of the sensor element is avoided while making a delay of sensor activation minimal.

6 Claims, 7 Drawing Sheets

U.S. PATENT DOCUMENTS

| | | | |
|---|---|---|---|
| 7,316,157 B2 * | 1/2008 | Ohsaki | 73/114.69 |
| 7,418,957 B2 * | 9/2008 | Abe | 123/697 |
| 2003/0070423 A1 | 4/2003 | Morinaga et al. | |

FOREIGN PATENT DOCUMENTS

| | | |
|---|---|---|
| JP | 62-022054 | 11/1994 |
| JP | 2002-048749 | 2/2002 |
| JP | 2003-083152 | 3/2003 |
| JP | 2003-269231 | 9/2003 |

* cited by examiner

SYSTEM FOR CONTROLLING EXHAUST GAS SENSOR HAVING HEATER

CROSS-REFERENCE TO RELATED APPLICATIONS

This application is based upon and claims benefit of priority of Japanese Patent Applications No. 2006-104856 filed on Apr. 6, 2006 and No. 2006-149163 filed on May 30, 2006, the contents of which are incorporated herein by reference.

BACKGROUND OF THE INVENTION

1. Field of the Invention

The present invention relates to a system for controlling exhaust gas sensor having a heater, the exhaust gas sensor being installed in an exhaust pipe of an internal combustion engine.

2. Description of Related Art

In an electronically controlled internal combustion engine, an exhaust gas sensor that detects oxygen density or an air-fuel ratio in exhaust gas is disposed in an exhaust pipe. An amount of fuel to be injected into the engine is controlled based on the oxygen density or the air-fuel ratio in the exhaust gas, so that the air-fuel ratio in the exhaust gas becomes equal to a target level. Generally, detection accuracy of the exhaust gas sensor is not sufficiently high before a temperature of the sensor reaches activation temperature. Therefore, the exhaust gas sensor is heated by a heater installed in the sensor.

Vaporized water that is formulated in combustion reaction of fuel and air is contained in the exhaust gas. The vaporized water in the exhaust gas condenses on the exhaust gas sensor when temperature in the exhaust pipe is low. If the exhaust gas sensor is heated to activate it by the heater immediately after the engine is started, the heated sensor element is partially cooled down by the condensed water. This may cause cracking of the sensor element.

To cope with this problem, JP-A-2003-269231 proposes to prohibit heating of the sensor until it is determined that water drops condensed on the sensor are scattered away by an exhaust gas flow in the exhaust pipe. In this system, however, activation of the sensor is delayed, and a feedback of the detected air-fuel ratio in the exhaust gas is delayed. This results in worsening in the emission quality.

JP-A-2003-328821 proposes a system, in which the exhaust gas sensor is heated immediately after the engine is started if it is determined that temperature in the exhaust pipe is high enough to prevent water condensation. On the other hand, a period of time, in which the heater operation is prohibited (referred to as a heater-off period), is set according to cooling water temperature if it is determined that temperature in the exhaust pipe is low. In this system, however, the heater-off period is not adequately set because it is set based on only the cooling water temperature. There is such a tendency that the heater-off period is set unnecessarily long, resulting in worsening the emission quality.

Further, JP-A-6-90167 proposes a system, in which a temperature sensor is installed in the exhaust gas sensor, and heating of the exhaust gas sensor is prohibited when the temperature of the exhaust gas sensor detected by the temperature sensor is lower than a predetermined level. In this system, however, it is necessary to install the temperature sensor in the exhaust gas sensor, making the exhaust gas sensor expensive.

Further, JP-A-2002-48749 proposes another system. In this system, an amount of heat or a temperature in the exhaust gas is calculated according to operating conditions of the engine, and a temperature of the exhaust pipe is calculated based on a mathematical heat conduction model between the exhaust pipe and the atmosphere. After the calculated temperature reaches a temperature at which no water condensation occurs, the exhaust gas sensor is heated by the heater. In this system, however, a computer load for calculating the exhaust pipe temperature becomes high, resulting in complication of a control system.

SUMMARY OF THE INVENTION

The present invention has been made in view of the above-mentioned problems, and an object of the present invention is to provide an improved system for controlling an exhaust gas sensor, in which cracking of the sensor element due to condensed water is prevented while activating the sensor without an unnecessary delay. Another object of the present invention is to realize such an improved system in a simple structure and at a low cost.

In an exhaust pipe of an internal combustion engine, a catalyzer for cleaning exhaust emissions is disposed. An exhaust gas sensor for detecting oxygen concentration in the exhaust gas is disposed in the exhaust pipe upstream of the catalyzer. An air-fuel ratio in the mixture supplied to the engine is controlled based on signals from the exhaust gas sensor. The exhaust gas sensor includes a heater for activating it. The exhaust gas sensor including its heater is controlled by a system according to the present invention.

If the exhaust gas sensor is heated to activate it while temperature of the exhaust gas is not sufficiently high, water vapor contained in the exhaust gas condenses on a sensor element of the sensor. If this occurs, the sensor element may be cracked because the heated sensor element is locally cooled by the condensed water. To prevent the sensor element from being cracked, the exhaust gas temperature is raised by retarding ignition timing of the engine.

The ignition timing is retarded to raise the exhaust gas temperature after the engine is started until the exhaust gas temperature reaches a predetermined level that prevents the water condensation. After the exhaust gas temperature reached such a level, the exhaust gas sensor is heated by the heater. Thus, cracking of the sensor element is avoided. Whether the exhaust gas temperature has reached the predetermined temperature may be determined based on an amount of intake air supplied to the engine after the engine is started. A period, in which the ignition timing is retarded, may be varied according to operating conditions of the engine.

The period, in which the sensor is not heated by the heater (referred to as a heater-off period), may be set various manners. For example, the heater-off period may be determined based on the cooling water temperature and a temperature difference between the cooling water and the atmosphere. The heater-off period is set longer as the cooling water temperature becomes lower to raise the exhaust gas temperature to a sufficient level. When the cooling water temperature is high, the heater-off period is set to a shorter period to avoid an unnecessary delay of activation of the exhaust gas sensor.

According to the present invention, the exhaust gas sensor is surely protected from being cracked due to water condensation while minimizing a delay of activation of the exhaust gas sensor. Other objects and features of the present invention will become more readily apparent from a better understanding of the preferred embodiments described below with reference to the following drawings.

DETAILED DESCRIPTION OF THE PREFERRED EMBODIMENTS

Figure 1:
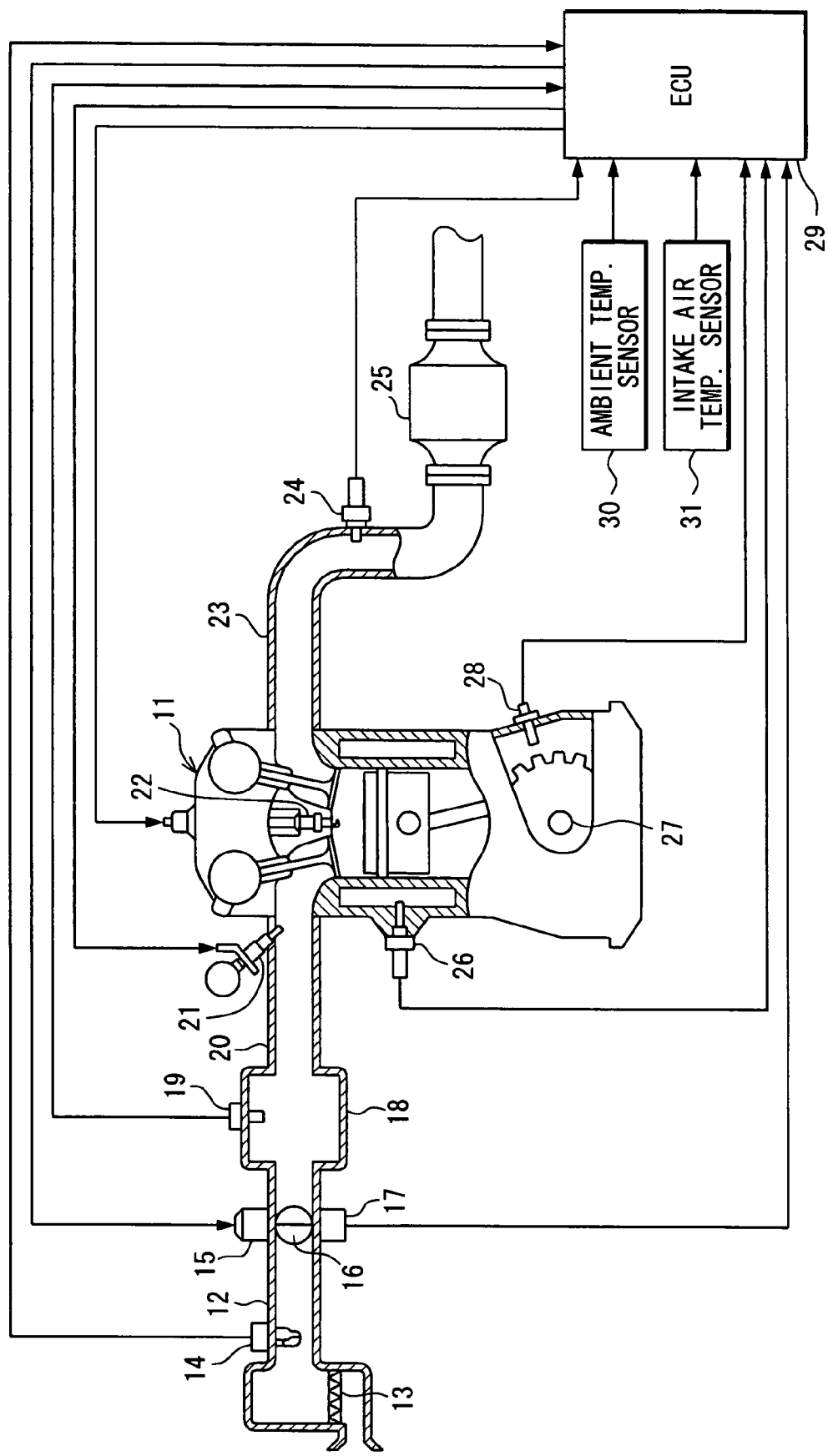
FIG. 1 is a cross-sectional view showing an entire structure of an engine control system including an exhaust gas sensor.

A first embodiment of the present invention will be described with reference to FIGS. 1-6. First, referring to FIG. 1, an entire structure of an engine control system including an exhaust gas sensor will be described. An internal combustion engine 11 has an intake pipe 12 and an exhaust pipe 23. An air cleaner 13 is connected to an upstream end of the intake pipe 12, and an airflow meter 14 for detecting an amount of intake air is provided downstream of the air cleaner 13. A throttle valve 16, an opening degree of which is controlled by a motor 15, and a throttle sensor 17 for detecting the opening degree of the throttle valve 16 are disposed downstream of the airflow meter 14.

A surge tank 18 is disposed downstream of the throttle valve 16, and a pressure sensor 19 for detecting pressure in the intake pipe is disposed in the surge tank 18. An intake manifold 20 connected to each cylinder is disposed downstream of the surge tank 18. A fuel injector 21 is installed in the intake manifold 20 at a position close to an intake port of each cylinder. A spark plug 22 corresponding to each cylinder is installed in a cylinder head of the engine. Air-fuel mixture is ignited by the spark plug 22.

An exhaust gas sensor 24, such as an air-fuel ratio sensor or an oxygen sensor, is installed in the exhaust pipe 23. A heater for heating the exhaust gas sensor is included in the exhaust gas sensor 24. A catalyzer 25 for cleaning the exhaust gas is connected to the exhaust pipe at a downstream position of the exhaust gas sensor 24. A sensor 26 for detecting temperature of cooling water and a crank angle sensor 28 are installed in a cylinder block of the engine. The crank angle sensor 28 generates pulse signals according to rotation of a crankshaft 27. Crank angles and rotational speed of the engine are detected based on the pulse signals generated by the crank angle sensor 28.

An ambient temperature sensor 30 and an intake air temperature sensor 31 are connected to an electronic control unit (referred to as ECU) 29. The ECU 29 including a microcomputer and a ROM performs engine control operation according to programs stored in the ROM. That is, an amount of fuel injected from the fuel injectors 21 and ignition timing of the spark plugs 22 are controlled based on signals fed to the ECU 29 from various sensors. An air-fuel ratio in the mixture gas supplied to the engine 11 is controlled so that it coincides with a target air-fuel ratio based on an air-fuel ratio or an oxygen density fed back from the exhaust gas sensor 24. The exhaust gas sensor 24 does not operate properly until it is heated to an activation temperature, e.g., 750° C. Therefore, the ECU 29 also controls temperature of the exhaust gas sensor 24 to activate it.

Water is formed by combustion of the air-fuel mixture in the engine, and the water thus formed is contained in the exhaust gas. When temperature of the exhaust pipe 23 is low (e.g., when immediately after the engine is started), the water condenses in the exhaust pipe 23 and adheres to the exhaust gas sensor. If the exhaust gas sensor is heated under this situation, a sensor element may be cracked or damaged because the heated sensor element is locally cooled by the condensation of the water. To cope with this problem, the temperature of the exhaust gas in the exhaust pipe 23 at an upstream portion of the exhaust gas sensor 24 is raised by retarding the ignition timing in the engine. More particularly, combustion in the engine is controlled so that a portion of combustion flames reaches the exhaust pipe 23 to raise the exhaust gas temperature. Thus, water contained in the exhaust gas is prevented from condensing.

Figure 2:
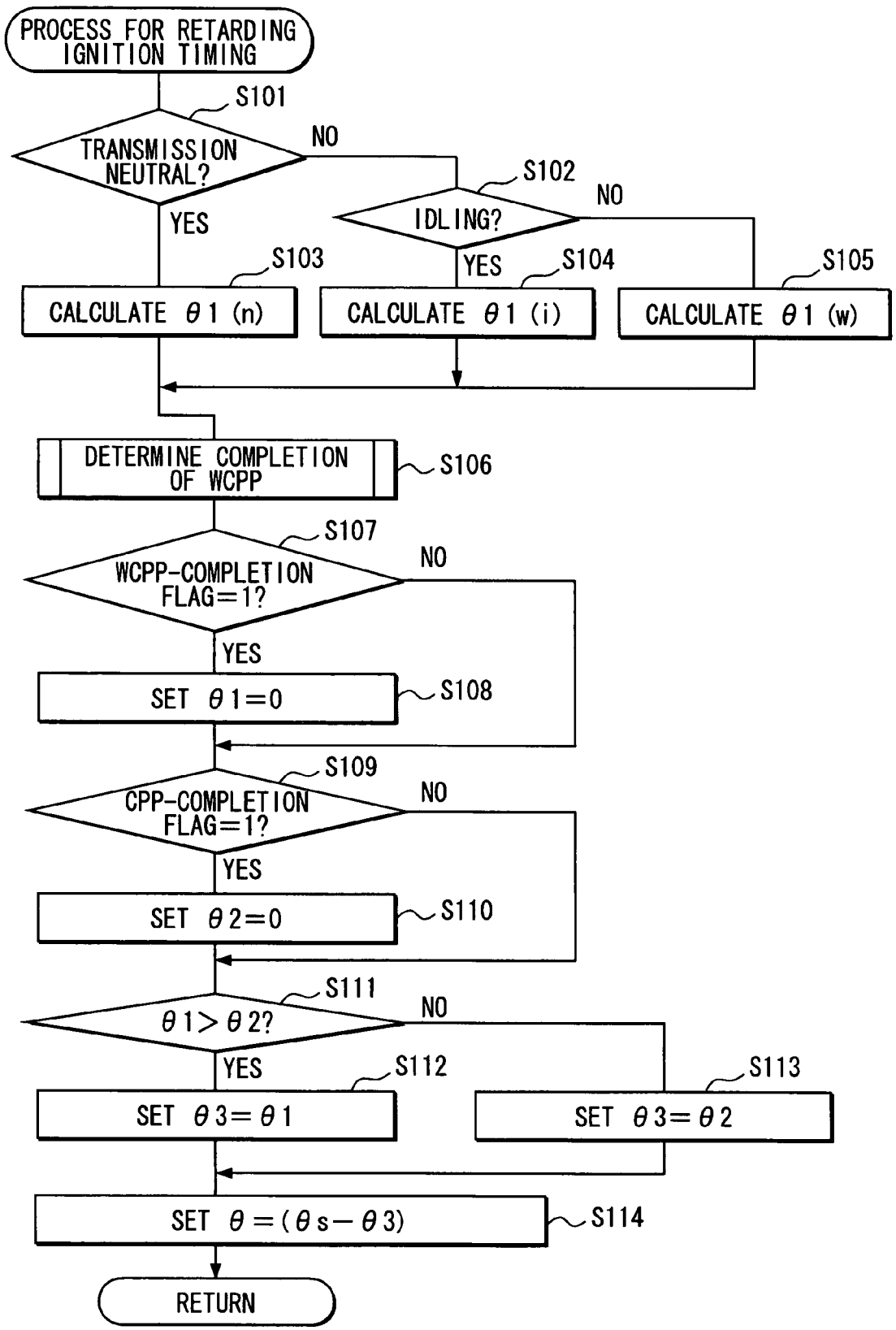
FIG. 2 is a flowchart showing a process for retarding ignition timing.
Figure 3:
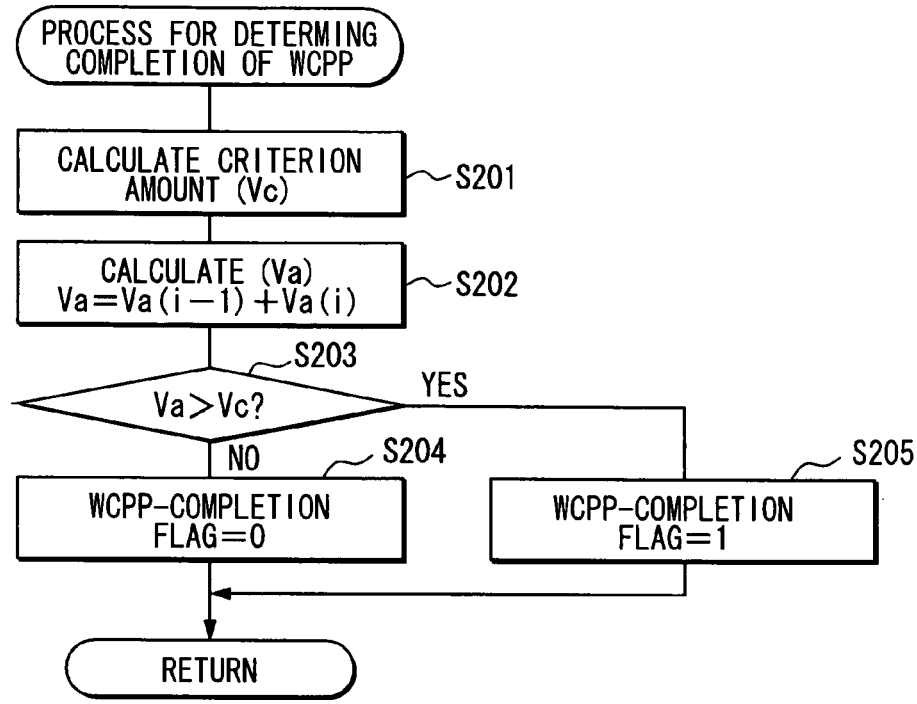
FIG. 3 is a flowchart showing a process for determining completion of a water-condensation-preventing process (WCPP), in a first embodiment of the present invention.

The process for retarding the ignition timing for raising the exhaust gas temperature will be explained in detail with reference to FIGS. 2 and 3. FIG. 2 is a flowchart showing a process for retarding the ignition timing, and FIG. 3 is a flowchart showing a process for determining completion of the water condensation preventing process (referred to as WCPP). The WCPP process is periodically performed while the ECU 29 is turned on.

At step S101 (FIG. 2), whether a shift lever is at a position (either one of a neutral position N or a park position P) or positions other than N and P is determined. If the lift lever is at N or P position, the process proceeds to step S103. At step S103, an amount of ignition timing retardation in terms of a crank angle (referred to as $\theta1(n)$), which is required for preventing water condensation when the shift lever is at N or P position, is calculated in reference to a map showing $\theta1(n)$ corresponding to engine speeds and amounts of intake air. If the shift lever is at positions other than N and P (drive position D or rear-drive position R), the process proceeds to S102, where whether the engine is idling or not is determined. If the engine is idling, the process proceeds to step S104. If not the process proceeds to step S105.

At step S104, an amount of ignition timing retardation in terms of a crank angle (referred to as $\theta1(i)$), which is required for preventing water condensation when the engine is idling, is calculated in reference to a map showing $\theta1(i)$ corresponding to engine speeds and amounts of intake air. At step S105, an amount of ignition timing retardation in terms of a crank angle (referred to as $\theta1(w)$), which is required for preventing water condensation when the engine is not idling (i.e., working), is calculated in reference to a map showing θ1(w) corresponding to engine speeds and amounts of intake air. In the series of steps S101-S105, the amount of ignition timing retardation θ1 required according to various operating conditions of the engine is calculated.

Then, the process proceeds to step S106, where whether the water condensation preventing process (WCPP) is completed or not is determined. If the WCPP is completed, the WCPP-completion flag is set (flag=1). The step S106 will be explained later in detail with reference to FIG. 3. At step S107, whether the WCPP-completion flag is set or not is determined. If the flag is set, the process proceeds to step S108, where θ1 is reset (θ1=0). If the WCPP-completion flag is not set at step S107, θ1 is maintained as it is. Then, process proceeds to step S109, where whether a catalyzer preheating process (CPP) is completed or not is determined. The catalyzer 25 is preheated by retarding the ignition timing, and if the CPP is completed, a CPP-completion flag is set (flag=1) under a process not explained here in detail.

If it is determined that CPP is completed at step S109, the process proceeds to step S110, where the amount of ignition timing retardation θ2 required in the CPP is reset (θ2=0). If the CPP is not completed, θ2 is maintained as it is. Then, at step S111, θ1 is compared with θ2 (θ1>θ2?). If θ1 is larger than θ2, the process proceeds to step S112, where a final ignition timing retardation amount θ3 is set to θ1 (θ3=θ1). If θ1 is not larger than θ2, the process proceeds to step S113, where θ3 is set to θ2 (θ3=θ2). Then, the process proceeds to step S114, where a final ignition timing θ is calculated by subtracting θ3 from a standard ignition timing θs (θ=θs−θ3).

In the process of retarding the ignition timing described above, during a period in which both of the WCPP and the CPP are performed in an overlapped manner, θ1 or θ2, whichever is larger, is adopted as the final ignition timing retardation amount θ3. Further, the ignition timing is retarded until the WCPP or the CPP, whichever is performed longer, is completed.

With reference to FIG. 3, the process of determining completion of the water condensation preventing process (WCPP) will be explained. This process is a sub-routine performed at S106 shown in FIG. 2. In this process, an accumulated amount of intake air (Va), which represents amount of heat given to the exhaust system, is calculated and compared with a criterion amount (Vc).

At step S201, the criterion amount Vc to be compared with Va is calculated in reference to a map showing Vc corresponding to the cooling water temperature when the engine is started. The criterion amount Vc represents an amount of heat which prevents cooling water condensation in the exhaust pipe 23 at an upstream portion of the exhaust gas sensor 24 without performing the WCPP. At step S202, the accumulated amount of intake air Va is calculated by adding an amount of present intake air Va(i) to a previously accumulated amount of intake air Va(i−1). That is, Va=Va(i−1)+Va(i). Va(i) is calculated based on signals from the airflow meter 14 and the intake pipe pressure sensor 19. In other words, the accumulated amount of intake air Va is obtained by incrementing the intake air volume Va(i) each time.

Then, at step S203, whether Va has become larger than the criterion amount Vc or not is determined. If Va is smaller than Vc, the process proceeds to step S204, where the WCPP-completion flag is not set (flag=0). When Va exceeds Vc, the process proceeds to step S205, where the WCPP-completion flag is set (flag=1). Then, the process comes to the end.

Figure 4:
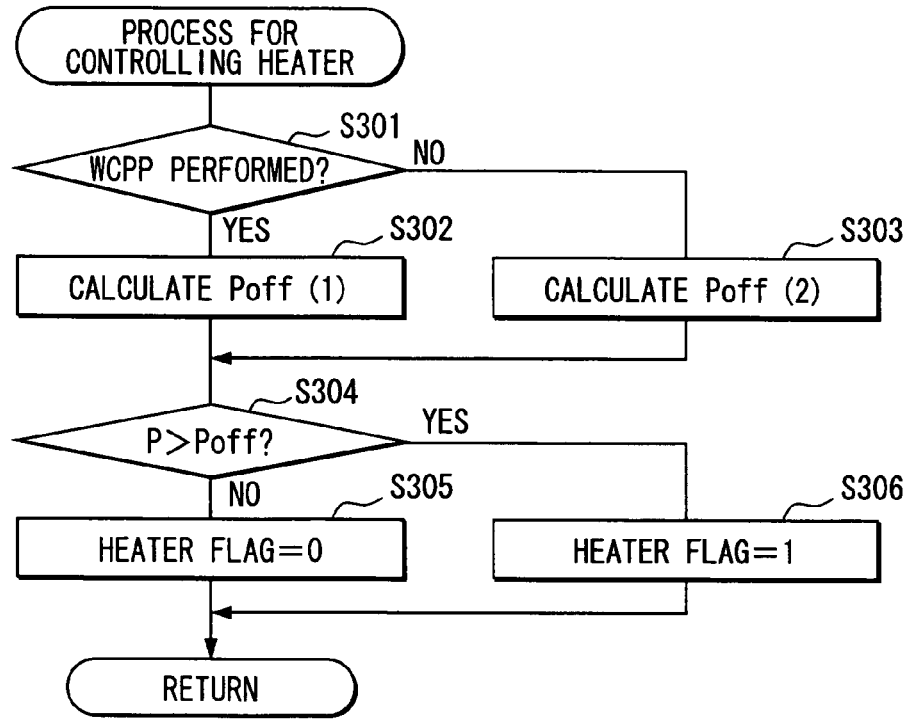
FIG. 4 is a flowchart showing a process for controlling a heater.

The heater of the exhaust gas sensor 24 is heated by a heater included therein according to a process shown in FIG. 4. The process for controlling the heater is periodically performed during a period in which the ECU 29 is operating. At step S301, whether the water condensation preventing process (WCPP) has been performed or not is determined. If the WCPP has been performed, the process proceeds to step S302. At step S302, a heater-off period Poff(1), in which the heater is turned off after the engine is started and which is applicable when the WCPP has been performed, is calculated according to the cooling water temperature at the engine start with reference to a map stored in the ECU 29. If the WCPP has not been performed, the process proceeds to step S303. At step S303, a heater-off period Poff(2), in which the heater is turned off after the engine is started and which is applicable when the WCPP has not been performed, is calculated according to the cooling water temperature at the engine start with reference to a map stored in the ECU 29.

Figure 5:
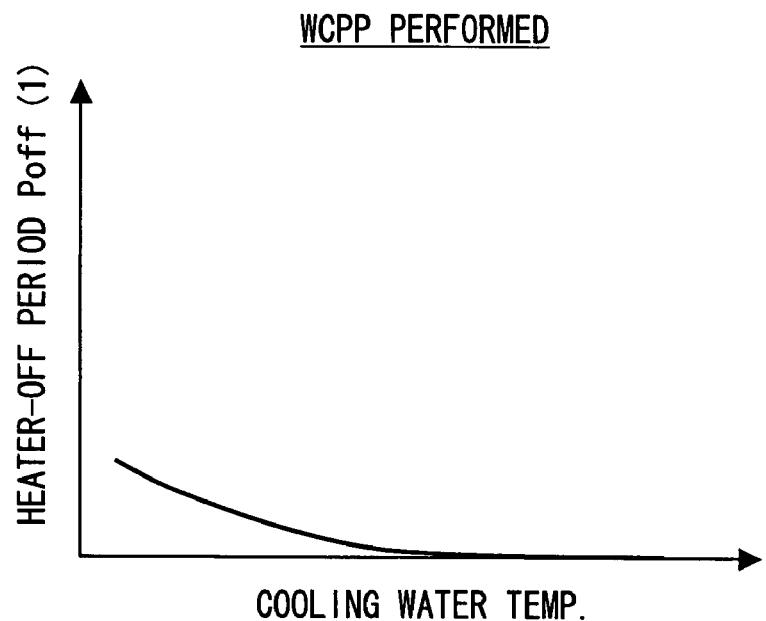
FIG. 5 is a graph showing a heater-off period Poff(1), when WCPP is performed, relative to the cooling water temperature.
Figure 6:
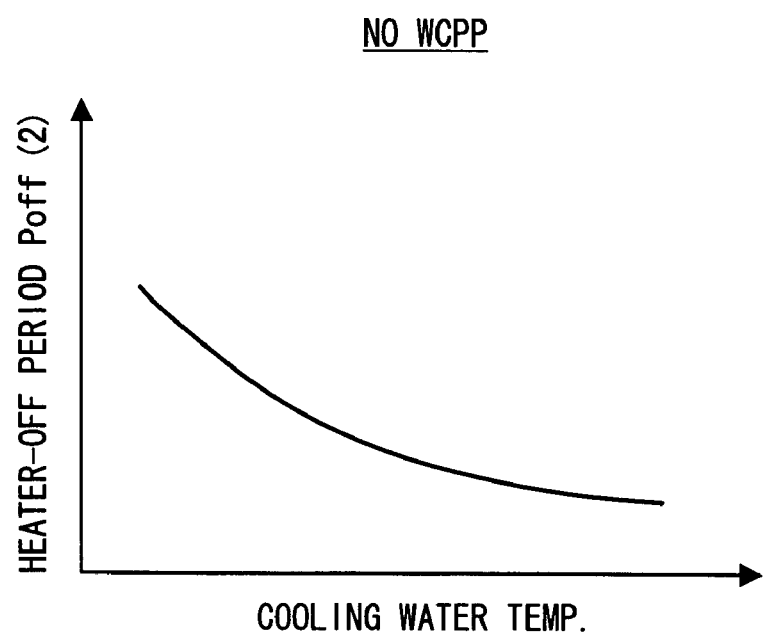
FIG. 6 is a graph showing a heater-off period Poff(2), when WCPP is not performed, relative to cooling water temperature.

As shown in FIGS. 5 and 6, Poff(1) is set to a shorter period than Poff(2) at the same cooling water temperature. Both of Poff(1) and Poff(2) are set so that they decrease as the cooling water temperature becomes higher.

Then, at step S304, whether a period P lapsed after the engine start is longer than the heater-off period Poff (either Poff(1) or Poff(2) fed at that time) is determined (P>Poff?). If P is not longer than Poff, the process proceeds to step S305, where a flag permitting heater operation is not set (flag=0). If P is longer than Poff, the process proceeds to step S306, where the flag permitting the heater operation is set (flag=1) Then, the process comes to the end.

Advantages attained in the first embodiment described above will be summarized. The exhaust gas is heated for a predetermined period of time after the engine is started by retarding the ignition timing to thereby prevent cooling water condensation on the exhaust gas sensor 24. After the temperature in the exhaust pipe 23 reaches a predetermined level, the exhaust gas sensor 24 is heated to activate it. Therefore, the sensor element is prevented from being cracked by the cooling water condensed thereon. Generally, when the exhaust gas sensor 24 is disposed in the exhaust pipe 23 at an upstream portion of the catalyzer 25, as is in the present invention, it is highly possible that the cooling water condenses on the sensor than when the sensor is positioned downstream of the catalyzer 25. Even when the sensor 24 is disposed upstream of the catalyzer 25 as is in the present embodiment, the cooling water condensation on the sensor 24 is surely prevented.

The heater is operated earlier when the water condensation preventing process (WCPP) is performed than when the WCPP is not performed. Therefore, the sensor 24 can be activated earlier by performing the WCPP. This means that the feedback control of the engine can be started earlier to thereby improve emissions.

The final amount of ignition timing retardation θ3 is set to an amount of θ1 (corresponding to WCPP) or θ2 (corresponding to CPP), which ever is larger. Therefore, the ignition timing is sufficiently retarded to cover both of the WCPP and the CPP. Further, since the ignition timing retardation is performed for a period of WCPP or CPP, whichever is longer, both processes are completely covered by a period in which the ignition timing retardation is carried out.

It is determined that the WCPP is completed when an accumulated amount of intake air after the engine start reaches a predetermined volume. The WCPP is not performed beyond a necessary period, but only for an appropriate period. Therefore, increase in fuel consumption and in engine noises is limited to a minimal amount. The amount of ignition timing retardation (θ1) for the WCPP is set according to operating conditions of the engine (e.g., idling or working). Therefore, θ1 is always set to an appropriate amount that fits the operating conditions of the engine.

Figure 7:
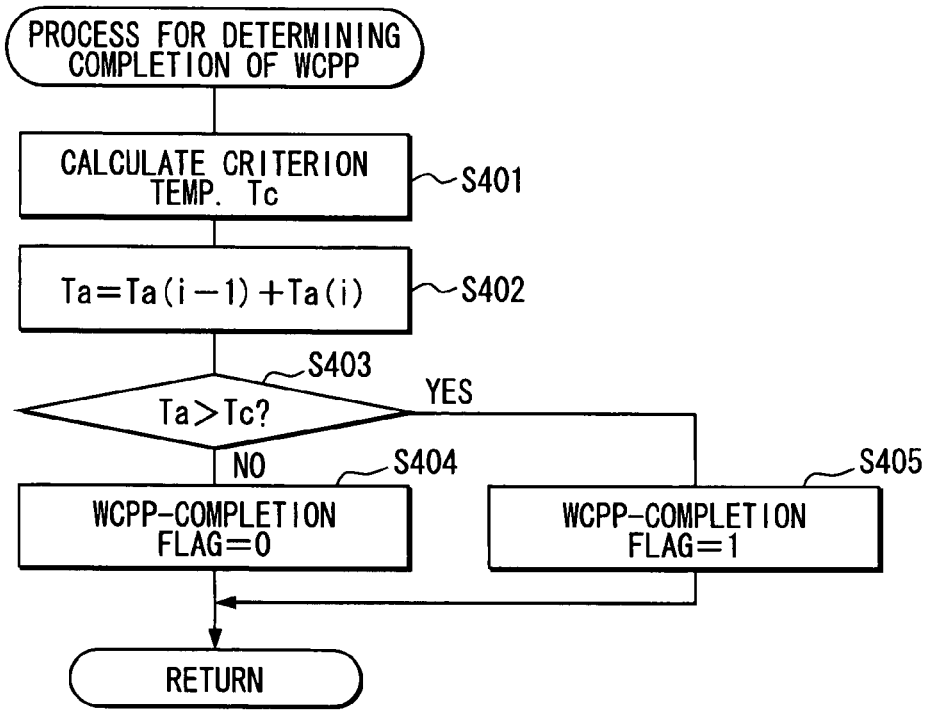
FIG. 7 is a flowchart showing a process for determining completion of WCPP, as a second embodiment of the present invention.

A second embodiment of the present invention will be described with reference to FIG. 7. In this embodiment, the completion of the WCPP is determined based on accumulated exhaust gas temperature. At step S401, a criterion temperature Tc in the exhaust gas, at which no water condensation occurs in the exhaust pipe 23 without performing WCPP, is calculated according to cooling water temperature at the engine start in reference to a map stored in the ECU 29. Then, at step S402, the accumulated temperature Ta in the exhaust gas is calculated (incremented) by adding a present temperature Ta(i) to an accumulated temperature Ta(i−1) up to a previous time. That is, Ta=Ta(i−1)+Ta(i).

Then, at step S403, whether the accumulated temperature Ta in the exhaust gas is higher than the criterion temperature Tc is determined (Ta>Tc?). If Ta is not higher than Tc, the process proceeds to step S404, where a flag indicating WCPP-completion is not set (flag=0). When Ta becomes higher than Tc, the process proceeds to step S405, where the WCPP-completion flag is set (flag=1).

In the second embodiment, the completion of the WCPP is surely determined based on the accumulated temperature in the exhaust gas. Therefore, the WCPP is performed for only a necessary period, and the increase in fuel consumption and in engine noises due to the WCPP is suppressed to a minimal level.

Figure 8:
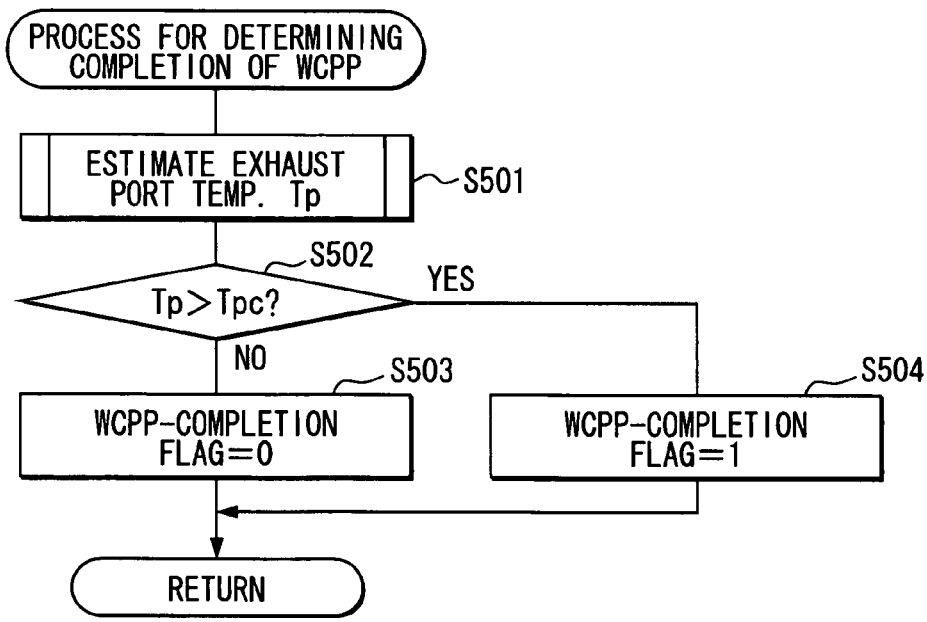
FIG. 8 is a flowchart showing a process for determining completion of WCPP, as a third embodiment of the present invention.

A third embodiment of the present invention will be described with reference to FIG. 8. In this embodiment, the completion of the WCPP is determined based on temperature at an exhaust port of the engine. At step S501, the exhaust port temperature Tp is estimated based on an amount of intake air, exhaust gas temperature and ambient temperature. At step S502, whether Tp is higher than a criterion temperature Tpc is determined. The criterion temperature Tpc is set to a temperature at which no water condensation occurs in the exhaust pipe 23 at an upstream portion of the exhaust gas sensor 24 without performing the WCPP.

If Tp is lower than Tpc, the process proceeds to step S503, where a flag indicating completion of the WCPP is not set (flag=0). When Tp becomes higher than Tpc, the process proceeds to step S504, where the flag indicating completion of WCPP is set (falg=1). Then, the process comes to the end. In this manner, the completion of the WCPP is appropriately determined, and increase in the fuel consumption and in engine noises is suppressed while preventing cooling water condensation in the exhaust pipe 23.

Though the completion of the WCPP is determined based on the temperature of the exhaust port of the engine in the third embodiment, it is possible to determined the completion of the WCPP based on temperature in the exhaust pipe 23 in the vicinity of the exhaust port of the engine. It is also possible to determine the completion of the WCPP based on two or more factors selected from Va, Ta and Tp.

A fourth embodiment of the present invention will be described with reference to FIGS. 9 and 10. In this embodiment, heating of the exhaust gas sensor 24 by the heater is not performed for a certain period of time after the engine is started in order to avoid cracking of the sensor element. In other words, heating of the sensor is delayed until the temperature in the exhaust pipe is elevated to a level at which no cooling water condensation occurs. Such period of time from the engine start to a time when heating of the sensor starts is referred to as a heater-off period Poff.

Figure 9:
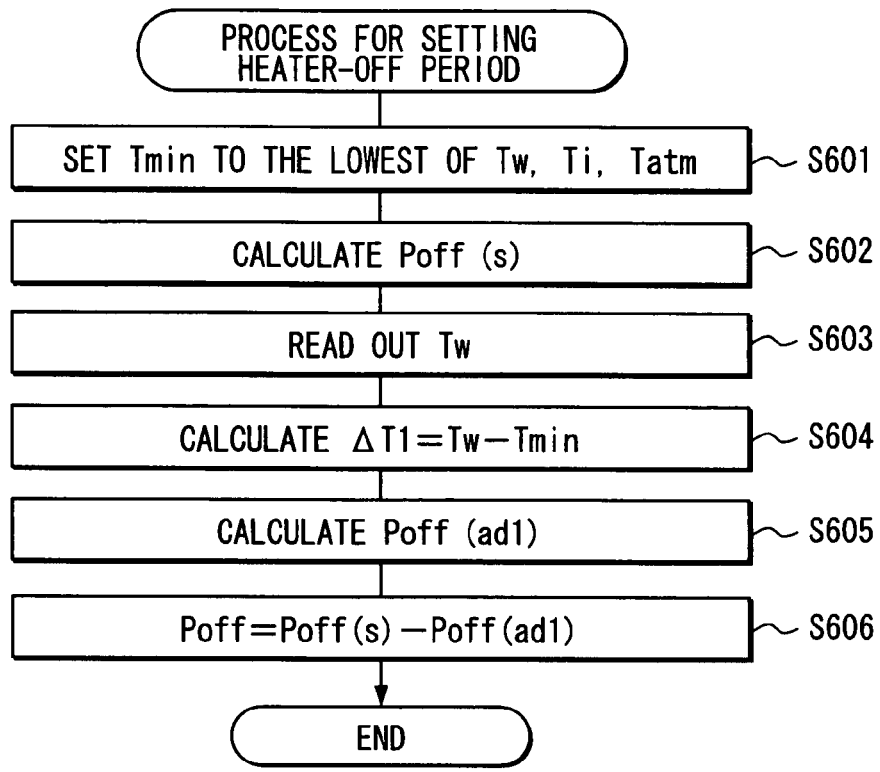
FIG. 9 is a flowchart showing a process for setting a heater-off period, as a fourth embodiment of the present invention.

Referring to FIG. 9, a process of setting the heater-off period Poff will be described. This process is performed when the engine is started. At step S601, temperature Tmin, which is the lowest among the cooling water temperature Tw, the intake air temperature Ti and the atmospheric temperature Tatm, is set. If the engine is started again only a short period after the engine was stopped, the cooling water temperature Tw at the engine start is higher than the atmospheric temperature Tatm or the intake air temperature Ti. Accordingly, Tatm or Ti is set to Tmin.

At step S602, a standard heater-off period Poff(s) is calculated according to Tmin based on a map or a formula stored in the ECU 29. Poff(s) becomes longer as Tmin becomes lower, because a long period is necessary to warm up the exhaust gas to a temperature at which the cooling water condensation does not occur. At step S603, the cooling water temperature Tw at the engine start is read out, and the process proceeds to step S604. At step S604, a temperature difference ΔT1 between Tw and Tmin is calculated (ΔT1=Tw−Tmin). In the case where the engine is restarted shortly after the engine was stopped, ΔT1 approximately equals to a difference between Tw and Ti or Tatm, because Tmin is approximately equals to Ti or Tatm in this case.

Figure 10:
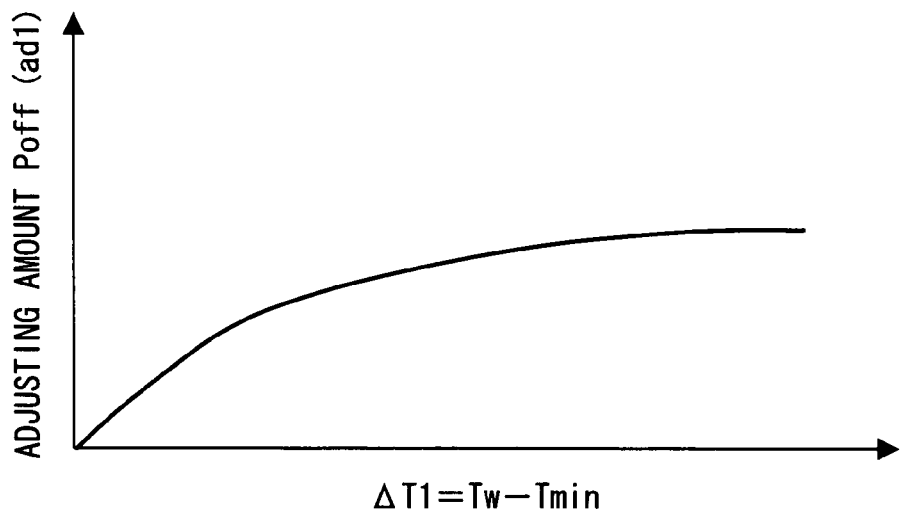
FIG. 10 is a graph showing an adjusting amount Poff(ad1) for a heater-off period relative to a temperature difference $\Delta T1$.

Then, at step S605, an amount Poff(ad1) for adjusting the standard heater-off period Poff(s) is calculated in reference to a map shown in FIG. 10. Poff(ad1) is larger as the temperature difference ΔT1 between Tw and Tmin becomes larger. At step S606, a final heater-off period Poff is calculated by subtracting Poff(ad1) from the standard heater-off period Poff(s). That is, Poff=Poff(s)−Poff(ad1). This means that the final heater off period Poff becomes shorter as the temperature difference ΔT1 becomes larger.

Since the temperature difference ΔT1 (=Tw−Tmin) approximately represents the exhaust pipe temperature at the engine start, the heater-off period Poff is set according to the temperature difference ΔT1. In this manner, the heater-off period Poff is set to a shorter period as the exhaust pipe temperature becomes high. Accordingly, the heater-off period Poff is set to an appropriate period that is necessary to warm up the exhaust gas to a temperature at which the cooling water does not condense. This means that the heater-off period is not set unnecessarily long, and accordingly adverse affects on the fuel consumption and engine noises due to setting the heater-off period are suppressed to a minimal level.

Further, it is not necessary to additionally use a sensor for detecting the exhaust pipe temperature, because the temperature difference between the cooling water temperature and the ambient or the intake air temperature is used as an amount representing the exhaust pipe temperature. Though the adjusting period Poff(ad1) is determined based on ΔT1 (=Tw−Tmin) in the fourth embodiment described above, it is also possible to determine Poff(ad1) based on a difference between Tw and Tatm or a difference between Tw and Ti.

A fifth embodiment of the present invention will be described with reference to FIGS. 11 and 12. In this embodiment, the adjusting period Poff(ad2) for adjusting the standard heater-off period Poff(s) is determined based on a temperature difference between the cooling water temperature Tw(stop) when a previous engine operation was stopped and the cooling water temperature Tw(start) when the engine is started this time.

Figure 11:
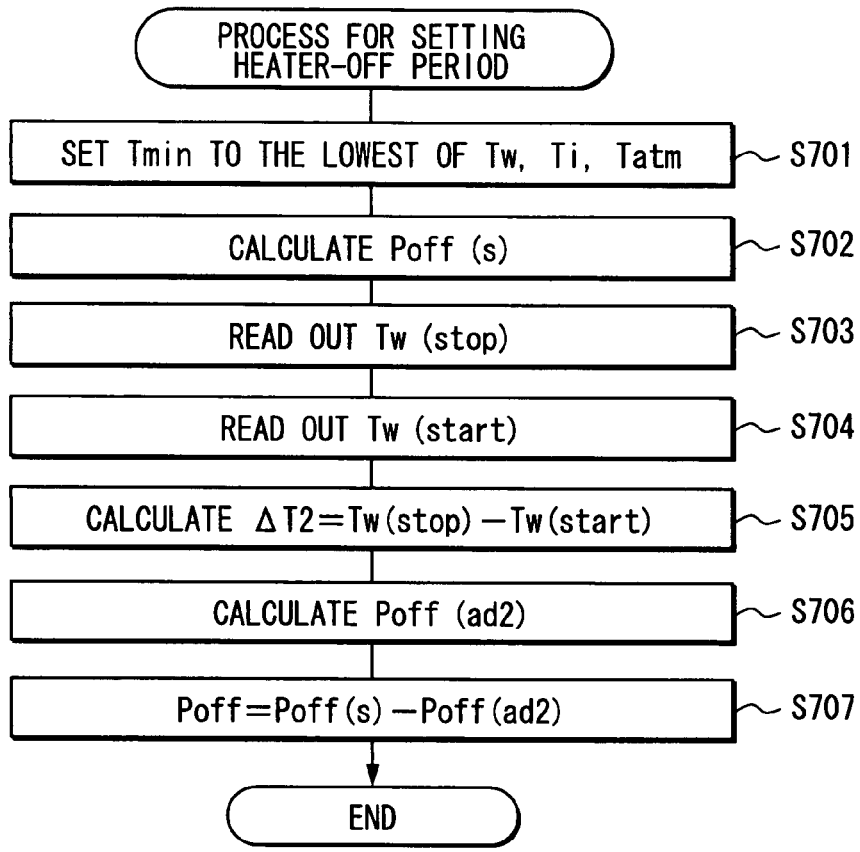
FIG. 11 is a flowchart showing a process for setting a heater-off period, as a fifth embodiment of the present invention.
Figure 12:
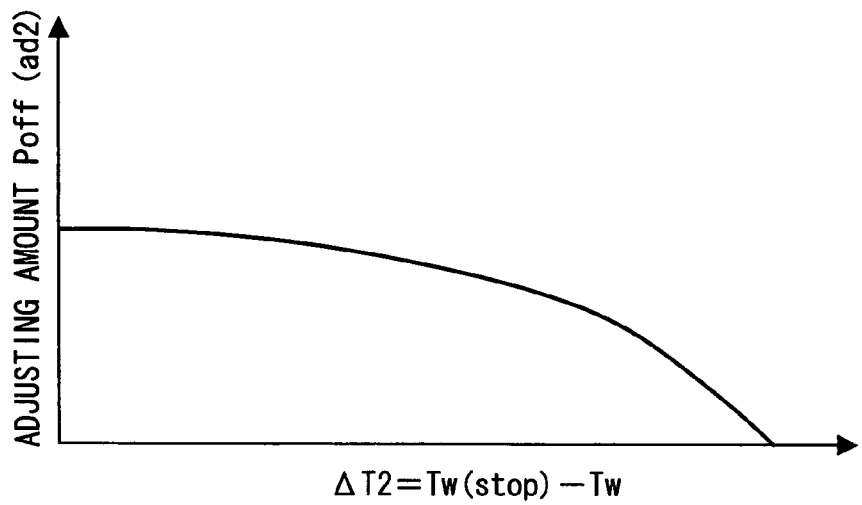
FIG. 12 is a graph showing an adjusting amount Poff(ad2) for a heater-off period relative to a temperature difference $\Delta T2$.

FIG. 11 shows a process for setting the heater-off period. At step S701, the lowest temperature among the cooling water temperature Tw, the intake air temperature Ti and the atmospheric temperature Tatm at the engine start is set as a minimum temperature Tmin. At step S702, a standard heater-off period Poff(s) that corresponds to Tmin is calculated based on a map or a formula stored in the ECU 29. Then, Tw(stop) and Tw(start) are read out at step S703 and step S704, respectively. Tw(stop) is detected immediately before the previous operation of the engine is terminated and is stored in a nonvolatile memory such as a backup RAM.

At step S705, a temperature difference $\Delta T2$ between Tw(stop) and Tw(start) is calculated ($\Delta T2=Tw(stop)-Tw(start)$). Then, at step S706, an amount Poff(ad2) for adjusting the standard heater-off period Poff(s) is obtained from a map stored in the ECU 29. The map is shown in FIG. 12. Then, at step S707, a final heater-off period Poff is calculated by subtracting Poff(ad2) from Poff(s). That is, Poff=Poffa(s)−Poff(ad2). As seen in the graph shown in FIG. 12, the adjusting amount Poff(ad2) becomes shorter as the temperature difference $\Delta T2$ is larger. Accordingly, the final heater-off period Poff becomes longer as the temperature difference $\Delta T2$ is larger.

Since the temperature difference $\Delta T2$ approximately represents the cooling water temperature at the engine start, the heater-off period is properly adjusted based on $\Delta T2$. Similar advantages as in the fourth embodiment are attained in this fifth embodiment, too.

In the fourth and fifth embodiments described above, the lowest of Tw, Ti and Tatm is set to the lowest temperature Tmin, and the standard heater-off period Poff(s) is calculated based on Tmin. However, the lowest of Tw and Tatm may be set to Tmin. Alternatively, the lowest of Tw and Ti may be set to Tmin.

While the present invention has been shown and described with reference to the foregoing preferred embodiments, it will be apparent to those skilled in the art that changes in form and detail may be made therein without departing from the scope of the invention as defined in the appended claims.

What is claimed is:

1. A system for controlling an exhaust gas sensor, the exhaust gas sensor including a heater and being disposed in an exhaust pipe of an internal combustion engine, the system comprising:
   a first means for preventing water condensation in the exhaust pipe at an upstream portion of the exhaust gas sensor by retarding ignition timing of the engine for a predetermined period after the engine is started to thereby elevate exhaust gas temperature in the exhaust pipe;
   a second means for heating a catalyzer for cleaning the exhaust gas by retarding ignition timing of the engine,
   a third means for determining a larger of (i) an amount of ignition timing retardation for preventing water condensation and (ii) an amount of ignition timing retardation for heating the catalyzer, and selecting and setting the determined larger amount as a final amount of ignition timing retardation,
   the amount of ignition timing retardation for preventing water condensation is calculated based on an engine speed and an amount of intake air, and
   the first means retards the ignition timing until an accumulated amount of intake air exceeds a criterion amount, an accumulated temperature in an exhaust gas exceeds a criterion accumulated temperature, or an exhaust port temperature exceeds a criterion exhaust port temperature.

2. A system for controlling an exhaust gas sensor, the exhaust gas sensor including a heater and being disposed in an exhaust pipe of an internal combustion engine, the system comprising:
   a first means for preventing water condensation in the exhaust pipe at an upstream portion of the exhaust gas sensor by retarding ignition timing of the engine for a predetermined period after the engine is started to thereby elevate exhaust gas temperature in the exhaust pipe;
   a second means for heating a catalyzes for cleaning the exhaust gas by retarding ignition timing of the engine,
   a third means for determining a longer of (i) a period in which the ignition timing is retarded for heating the catalyze and (ii) a period in which the ignition timing is retarded for preventing water condensation, wherein the ignition timing is retarded for the determined longer period,
   the period in which the ignition timing is retarded is calculated based on an engine speed and an amount of intake air, and
   the first means retards the ignition timing until an accumulated amount of intake air exceeds a criterion amount, an accumulated temperature in an exhaust gas exceeds a criterion accumulated temperature, or an exhaust port temperature exceeds a criterion exhaust port temperature.

3. The system for controlling an exhaust gas sensor as in claim 1, wherein:
   the exhaust gas sensor is positioned in the exhaust pipe upstream of the catalyzer.

4. The system for controlling an exhaust gas sensor as in claim 1, wherein:
   the exhaust gas sensor is heated by the heater earlier after the engine is started when the first means for preventing water condensation is operated than when it is not operated.

5. A method of controlling an exhaust gas sensor, the exhaust gas sensor including a heater and being disposed in an exhaust pipe of an internal combustion engine, the method comprising:
   preventing water condensation in the exhaust pipe at an upstream portion of the exhaust gas sensor by retarding ignition timing of the engine for a predetermined period after the engine is started to thereby elevate exhaust gas temperature in the exhaust pipe;
   heating a catalyzer for cleaning the exhaust gas by retarding ignition timing of the engine,
   determining a larger of (i) an amount of ignition timing retardation for preventing water condensation and (ii) an amount of ignition timing retardation for heating the catalyzer, and
   selecting and setting the determined larger amount as a final amount of ignition timing retardation, wherein:
   the amount of ignition timing retardation for preventing water condensation is calculated based on an engine speed and an amount of intake air, and
   the ignition timing is retarded until an accumulated amount of intake air exceeds a criterion amount, an accumulated temperature in an exhaust gas exceeds a criterion accumulated temperature, or an exhaust port temperature exceeds a criterion exhaust port temperature.

6. A method of controlling an exhaust gas sensor, the exhaust gas sensor including a heater and being disposed in an exhaust pipe of an internal combustion engine, the method comprising:
   preventing water condensation in the exhaust pipe at an upstream portion of the exhaust gas sensor by retarding ignition timing of the engine for a predetermined period after the engine is started to thereby elevate exhaust gas temperature in the exhaust pipe;

heating a catalyzer for cleaning the exhaust gas by retarding ignition timing of the engine, determining a longer of (i) a period in which the ignition timing is retarded for heating the catalyser and (ii) a period in which the ignition timing is retarded for preventing water condensation, wherein:

the ignition timing is retarded for the determined longer period, the period in which the ignition timing is retarded is calculated based on an engine speed and an amount of intake air, and the ignition timing is retarded until an accumulated amount of intake air exceeds a criterion amount, an accumulated temperature in an exhaust gas exceeds a criterion accumulated temperature, or an exhaust port temperature exceeds a criterion exhaust port temperature.

* * * * *